United States Patent [19]

Gittleman

[11] Patent Number: 5,641,287
[45] Date of Patent: Jun. 24, 1997

[54] DENTAL TOOL GUIDANCE TEMPLATE AND METHOD

[76] Inventor: Neal B. Gittleman, 15 Greenway Plz. #1D, Houston, Tex. 77046

[21] Appl. No.: 328,907

[22] Filed: Oct. 25, 1994

[51] Int. Cl.$^6$ ............................................. A61C 3/00
[52] U.S. Cl. ............................................. 433/75; 606/96
[58] Field of Search .......................... 433/72, 75, 76; 606/96, 98

[56] References Cited

U.S. PATENT DOCUMENTS

| | | | |
|---|---|---|---|
| 569,210 | 10/1896 | Land | 433/75 |
| 3,011,259 | 12/1961 | Baum | 433/75 |
| 3,955,558 | 5/1976 | Fuisz | 606/96 |
| 4,109,382 | 8/1978 | Koch | 433/176 |
| 4,325,373 | 4/1982 | Slivenko et al. | 433/72 |
| 5,141,513 | 8/1992 | Fortune et al. | 606/96 |
| 5,306,278 | 4/1994 | Dahl et al. | 606/96 |

*Primary Examiner*—John J. Wilson
*Attorney, Agent, or Firm*—Ezra L. Schacht

[57] ABSTRACT

An apparatus and method for the steady and accurate placement of a narrow smooth-walled slot in a bone structure by means of a hand held guidance template with a transparent slide to perpendicularly restrain a rotating cutting bit of a hand held tool while the transparent slide is drawn along a slot in the guidance template. The template is held in place with a light force through the guidance template handle and accurately positioned by means of serrated depth stops and perforated extensions bonded to a quick-setting resilient polymer conforming to the contour of the bone structure. Prevented from non-axial motion, the rotating cutting bit is plunged deeper to route a narrow smooth-walled slot in the bone structure. The primary use envisioned for the guidance template is in the accurate placement of an endosteal inline plate in the structural bone of the mouth for the attachment of permanent dental prosthetics. Fiber optic illumination and tubes for the delivery of sterile saline wash and suctioned removal of debris are mounted on the guidance template. A snap-in drilling guide fits the guidance slot for subsequent accurate placement of multiple holes to accommodate permucosal extensions of the inline plate.

5 Claims, 5 Drawing Sheets

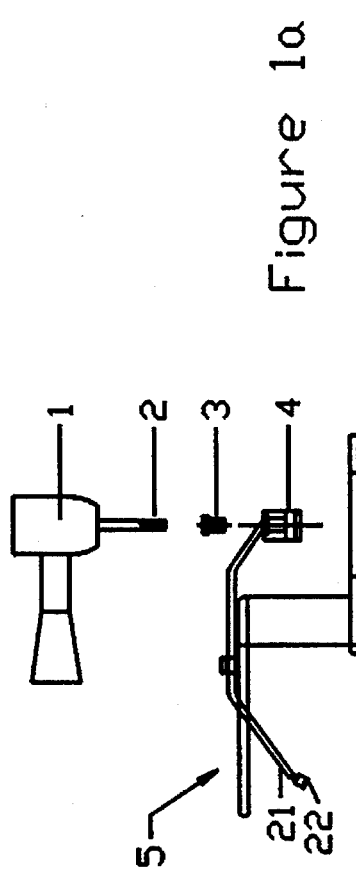
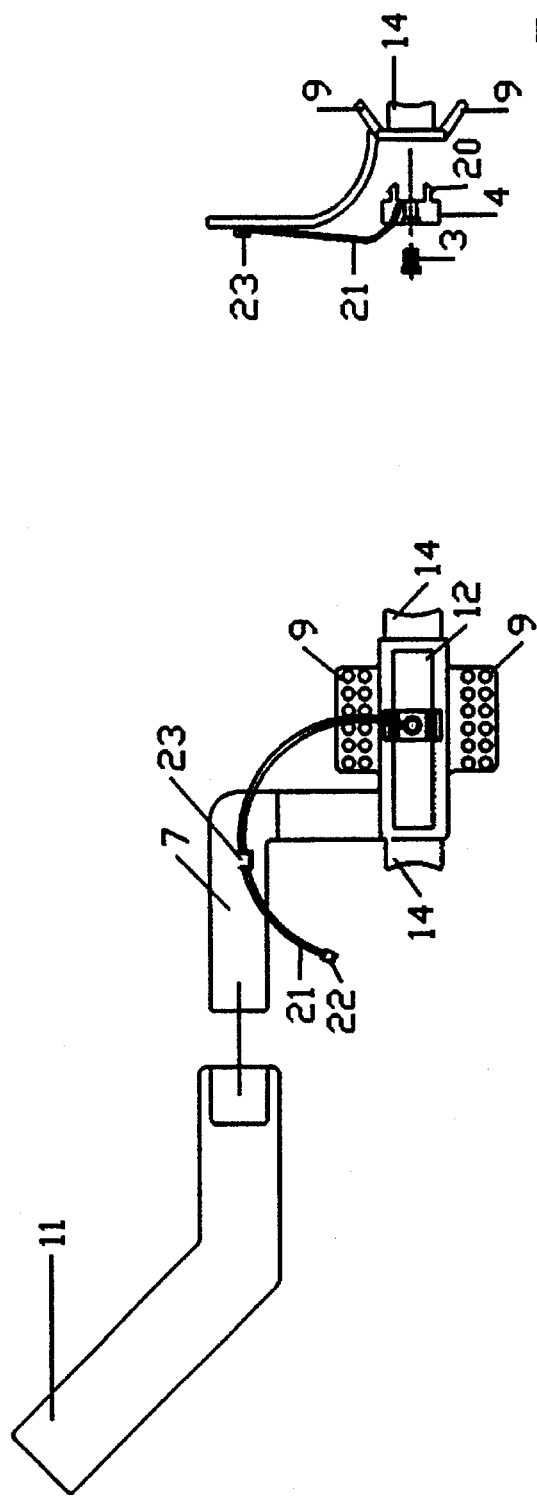

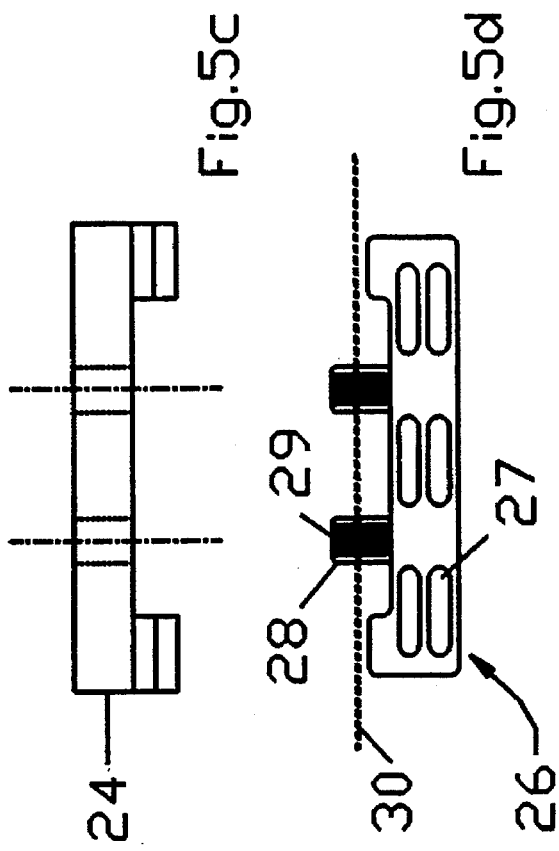
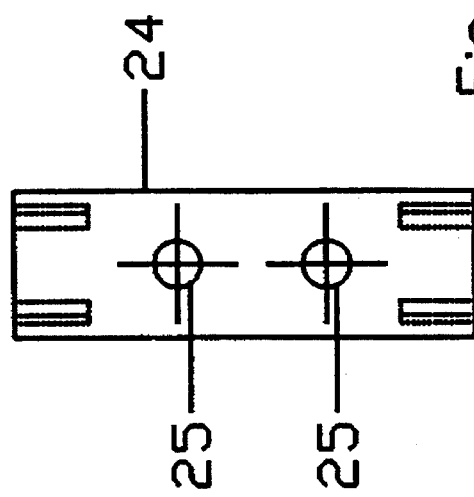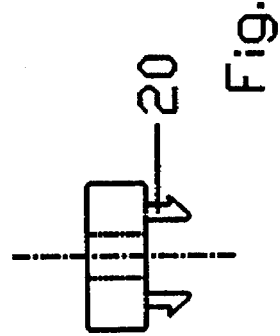

DENTAL TOOL GUIDANCE TEMPLATE AND METHOD

DESCRIPTION OF THE CURRENT TECHNOLOGY

The need to provide a firm support for prosthetic replacements for adjacent teeth in the mandible or maxillary region is now being met by biocompatible metal implants anchored within the maxillary or mandibular bone by means of posts or plates. The posts made from a tough, non-corroding titanium alloy are installed in a predrilled cylindrical hole. Over time the post is incorporated in the growing replacement bone and acts as a support for an artificial tooth. Several posts can be installed for a bridge of replacements. Limited by the length of the cylinder and the depth of the bone structure available for implantation, the post offers less implant-bone surface bonding area than a thin long inline plate implant. In addition, the inline plate implant can be fitted into a slot in the bone structure in excessively narrow sections of the mandible or maxilla that might compromise lateral strength of the bone with a cylindrical post. Slots in the inline plate allow the bone to grow through the plate for increased stability and strength. Coatings of bio-compatible hydroxylapatite, the mineral substance of bone, are applied to the posts and inline plates for a more intimate adherence of live, dense bone to the implant alloy.

THE NATURE OF THE INVENTION

Where it is relatively simple to drill a cylindrical hole in bone for the installation of a cylindrical post, difficulty arises in the precise method of making the slot in bone to install an inline plate implant. Guiding a handheld tool with a rotating cutting head with the precision necessary to create a narrow, smooth-walled slot of uniform depth is an arduous and time consuming task for those practiced in the art of dentistry. Care must be taken not to damage the major neurovascular bundle in the mandible. A carefully made slot in the bone allows for a more intimate contact between bone and the prosthetic coating for a strong quick bond that helps prevents the ingress of undesirable fibrous tissue.

The apparatus described herein answers the need to provide a steady guide for the careful, quick and accurate placement of a narrow slot in bone for the installation of a plate implant. The slot is typically, 25 mm long, less than 2 mm wide and 8 to 12 mm deep, though other sizes are available. The inline plate can be flat or curved to conform to the front regions of the mandible or maxilla. The apparatus described in this specification will guide the handheld tool to conform to the required length and curvature of the slot.

PRIOR ART

In U.S. Pat No. 4,109,382 Enossal Implant, Werner Lutz Koch inventor, the method described requires a pilot hole in the bone for the oblong template fitting pin before the template can be accurately positioned. The Koch patent requires a special fitting collar around the cutting bit, i.e., "the axial stop surface provided on the reamer", while the present invention uses standard surgical cutting bits of standardized lengths to limit the depth of penetration into the bone.

Further, the Koch method requires a "partially reamed slit" be made after the "oblong template" has been placed in the bone in order that a "sword" be placed to prevent the template from "twisting" around the "oblong template fitting pin." This "sword" is placed and removed several times to retain the alignment of the template while the bone is slotted. At each removal and insertion of the sword, the opportunity for the slit cut in the bone to deviate from a straight line increases. This "twisting" even if slight, would require the slot in the bone to be wider to compensate for any irregularities and thus compromise the intimate fit between implant plate and live bone. In addition, the first "partially reamed slit" in the bone is made while the template is not prevented from rotating, in that no slot yet exists to accommodate the anti-rotation "sword".

The advantages of the present invention are manifest in the one time placement of the dental guidance template and the use of standard cutting bits to quickly and accurately make a straight inline slot in bone. Anchoring the template's perforated projections or "wings" with a quick setting polymer in intimate contact with mouth and bone structures, coupled with the compressive pressure supplied through the handle of the template constitute a novel method and apparatus for this surgical application. In addition, the current invention allows for greater visibility by the use of transparent materials.

BRIEF DESCRIPTION OF THE DRAWINGS

FIG. 1a presents an elevated exploded view of the dental guide template;

FIG. 1b is a plan view of the dental guide template and its handle;

FIG. 1c is the sectional view taken along line A—A through the dental guide template in FIG. 1b;

FIG. 2b is the plan view of the apparatus in FIG. 2a;

FIG. 5a is a plan view of screw post drilling template;

FIG. 5b show the end elevation of the screw post drilling template; and

FIG. 5c is the side elevated view of the screw post drilling template and FIG. 5d is a side elevated view of a typical endosteal inline plate implant.

DETAILED DESCRIPTION OF ONE OR MORE OF THE PREFERRED EMBODIMENTS

Figure 2A:
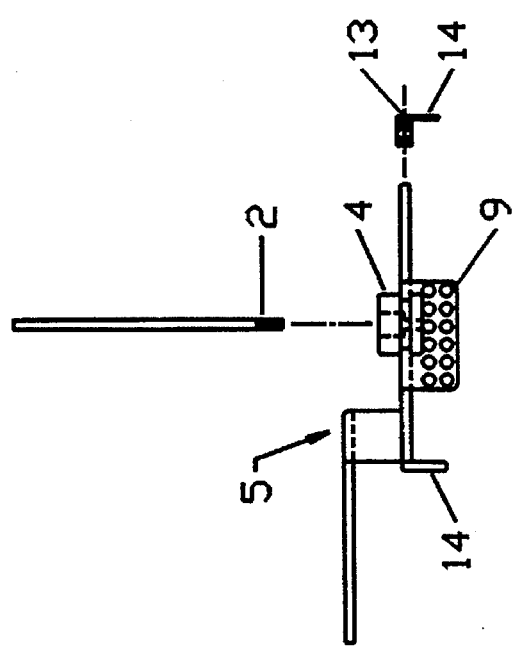
FIG. 2a demonstrates an elevated view of a forked ended dental guide template with slide bushing and retaining clip.

Referring to FIGS. 1a, 1b and 1c the apparatus consists of a hand held dental guide template 5 made of stainless steel or other suitable material with a slotted end 12 confining a sliding bushing acting as a slide 4 to confine a cutting bit 2 to the centerline of the required slot in the bone. The slide 4 has a countersunk center hole with a low friction, shoulder bushing 3 of Teflon™ or other low friction material, to act as a confining vertical guide for the rotating cutting bit 2 extending from a motor driven, hand held, rotary cutting tool 1. The cutting bit 2 is raised and lowered by hand within the close fitting cylindrical hole in the shoulder bushing 3 while the slide 4 is pushed or pulled along the guide template slot 12.

In this embodiment of the invention, the slide 4 is made of a suitably transparent material such as Acrylic or Polycarbonate with a Teflon™ or Delrin™ low friction shoulder bushing installed within a central hole to act as a low friction, confining guide for the rotating cutting bit 2. The transparent material allows the fiber optic light pipe ends within most hand held rotary cutting tools 1 to illuminate the bone being cut. A small flexible tube 21 for irrigating with saline solution is installed through the slide to flush debris from the milled slot in the bone and to cool the tool to prevent overheating the tissue. The other end of the flexible irrigation tube 21 is suitably clamped to the guide template tang 7 by suitable means 23 and terminated with a Luer-Lok™ or other connection fitting 22 to a source of sterile saline solution.

Figure 4A:
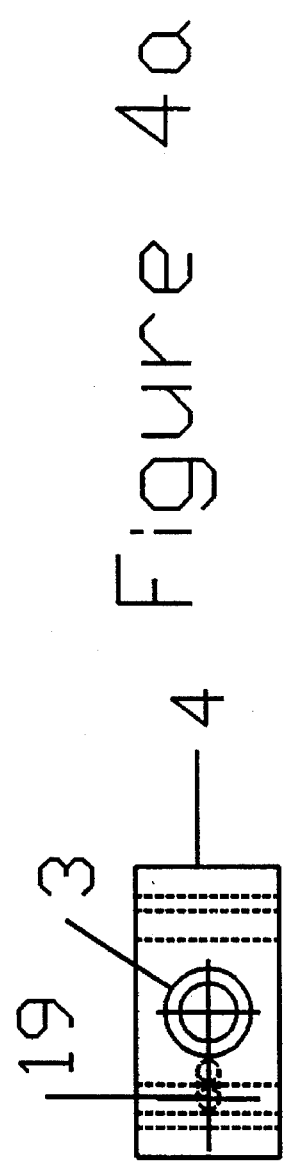
FIG. 4a shows a detailed plan view of slide element.
Figure 4C:
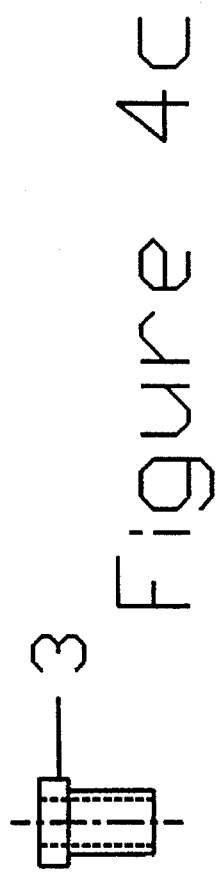
FIG. 4c is an elevated view of the low friction shoulder bush.
Figure 4B:
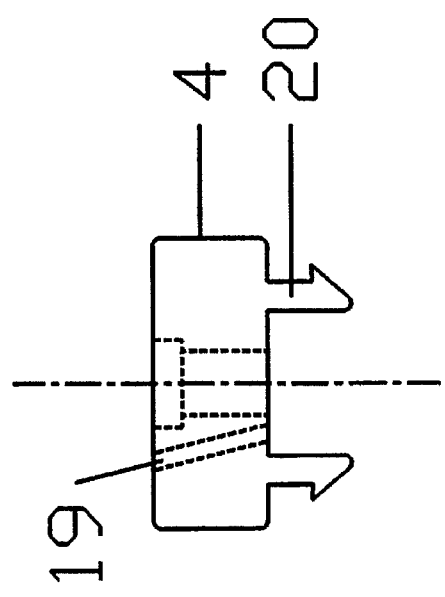
FIG. 4b is a side elevation of the slide.

One method of installing the slide 4 within the slot 12 in the guide template 5 is by means of flexible, barbed, cantilevered projections 20 that snap into the confining slot with just enough clearance to allow the slide to be moved freely along the guide template slot 12 yet hold the cutting bit 2 perpendicular to the guide template face. The central Teflon™ or Delrin™ low friction shoulder bushing 3 can be fitted in a countersunk hole through the transparent slide 4 and fixed in place by thermally deforming the transparent slide 4 near the countersunk hole. Referring to FIGS. 4a and 4b, in this embodiment shows channel hole 19 where saline irrigation tube 21 is fitted. FIG. 4c is a detailed view of the low friction shoulder bushing 3.

A reversible handle 11 friction fits over the slightly tapered end of the guide template tang 7. This allows the tool to be turned to serve the left or right hand at a comfortable angle. The dental guide template in the drawings will serve lower right or the upper left areas of the mouth. A "mirror image" template will serve the other side of the mouth.

Figure 3B:
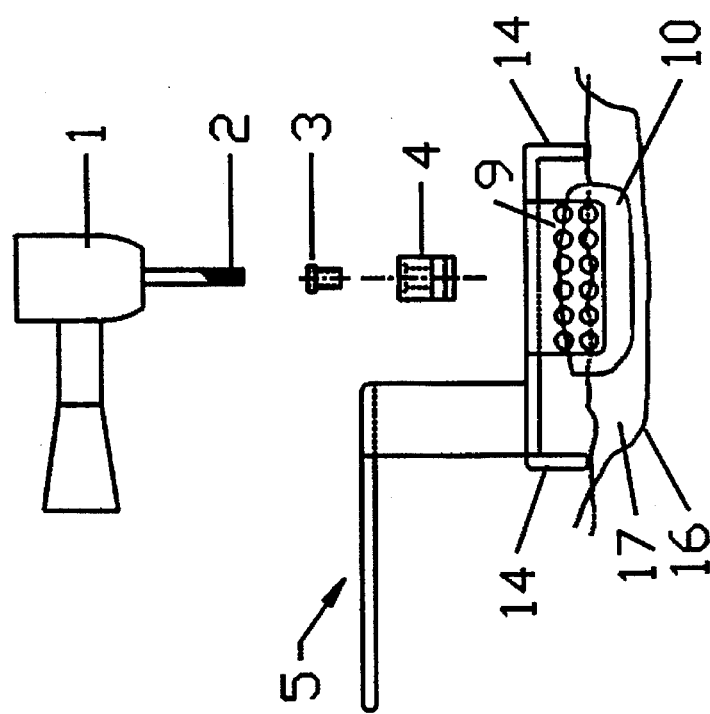
FIG. 3b is an elevated side view of the same view.
Figure 3A:
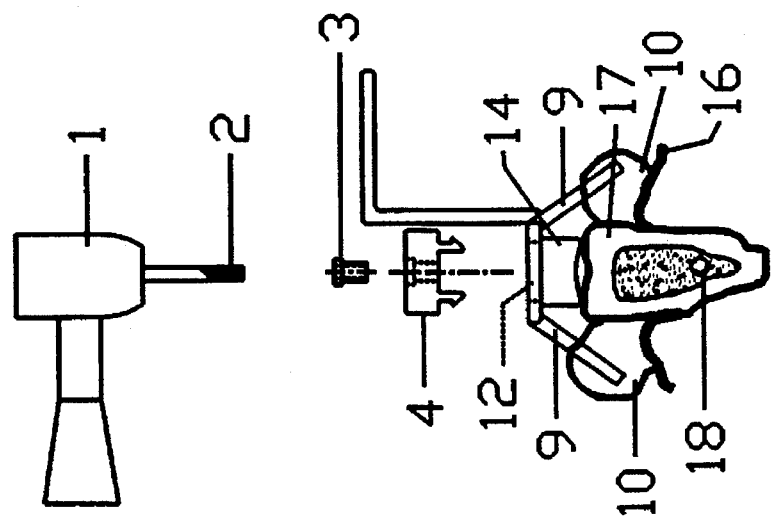
FIG. 3a is an elevated sectional view of the dental guide template shown in direct application to the surgical site.

FIGS. 3a and 3b illustrate the handheld guide template 5 equipped with a set of perforated side projections or "wings" 9 which act to anchor a resilient polymer compound 10. This polymer compound 10 is allowed to conform to the structures 16 in the mouth and around the exposed bone 17 before setting up. When the guide template is accurately placed, this compound 10 congeals to a pliable, rubbery mass to secure the guide template. Simple pressure of a few kilograms acting through the guide template handle 11 guarantees that the guide template 5 cannot slip during the slotting of the bone.

Stop tabs 14 exhibit a curve on the outer edge to facilitate rotation around the mesio-distal axis to place the slot in the bone in correct alignment. The curved outer edge can be formed to a "knife-like" edge or serrated, multi-pointed edge like a saw blade to provide additional purchase on the bone surface with the pressure transferred through the handle 11. One or both of the stop tabs 14 may be of adjustable length to incline the implant plate 26 to the surface of the bone 30, as in those bone areas exhibiting uneven surface characteristics from bone loss or resorption or in upward curve near the angle of the mandible. In unusual bone morphologies, added purchase on the bone may be made with adjustable set screws threaded through holes located in the perforated side projections or "wings" 9. These set screws can end in a point for better purchase to the bone.

The cutting bit 2 used to make the slot in the bone is typically 1.6 mm in diameter with a cutting head of the same size. The length of the cutting head should be long enough to make the in a reasonable number of strokes or passes, yet short enough to project below the shoulder bushing 3 to prevent damage to the internal bearing surface of the Teflon shoulder bushing 3, which is spaced above the bone surface by means of stop tabs 14 bent at right angles to the plane of the guide template slot 12. The stop tabs 14 are of the correct length to guarantee a fixed maximum depth of the slot in the bone for a given length cutting bit 2 thus avoiding the neurovascular bundle 18 in the mandible as determined by x-ray or other means.

A bend and a lateral offset in the tang 7 of the dental guide template 5 beginning near the template slot 12 will avoid any remaining teeth or prostheses.

Figure 2B:
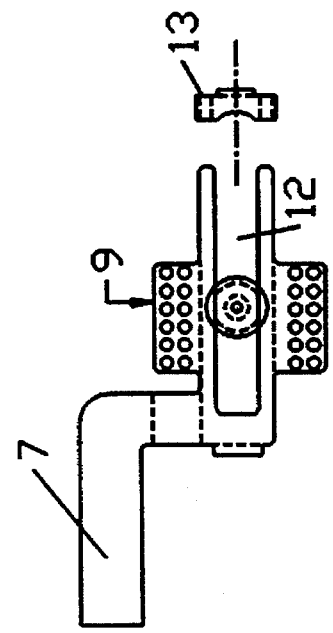
Figure 2C:
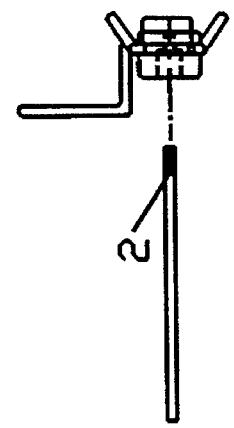
FIG. 2c is a sectional view taken along line A—A of drawing FIG. 2b.

In another embodiment of the apparatus, in FIG. 2a through 2c, the guide template slot ends in a fork 12 for easy placement of the slide bushing 4. A retainer clip 13 with detente and end stop 14 slides over the end of the fork to limit the length of the slot. It is intended that, in this embodiment, that the softer Teflon slide bushing 4 be replaced at minimum cost for each procedure. The slide 4 is equipped with a set of parallel, flat side grooves for restraint and guidance along the fork.

The dental guide template is designed to be blanked out of sheet stainless steel by press, chemical milling or by laser cutting. The bends can be made in a press brake. A vibratory barrel abrasive finishing technique can be used to improve the final finish of the part. The tool is easily sterilized since it is made from heat resistant materials and has no hidden recesses.

The transparent slide can be replaced for each procedure and can be solution sterilized. If laser or chemical machining of the stainless steel is used, the tool can be customized to each individual application, matching the slot length and curvature exactly to custom designed implant plates. The individualized drawing pattern can be transmitted to the fabricator by modem over the telephone lines, entered into the automated laser cutter and duplicated exactly to individual specifications.

Another adaptation of the invention has the means for delivery of sterile saline wash and suctioned removal of debris by means of attachable stainless steel fittings on the tool. In addition, fiber optic light pipes can be attached to provide additional local illumination.

Another embodiment of this tool has the tang 7 of the tool at right angles to the template slot 12. The right angle tang would allow the dentist to more comfortably guide a handheld cutter in making a slot for an inline plate implant for the front of the mouth.

Other techniques of manufacture can include molding the guide template from disposable plastic with the addition of stiffening, ribs. If the guide template 5 is fabricated of transparent material, the dentist will have a better view of the condition surrounding structures. A tube can be molded into the guide template to deliver saline irrigation fluids. Additional clips and channels can be molded into the plastic to attach fiber optic light guides for better illumination.

Referring to drawings FIGS. 5a through 5d, after the slot is cut to the required depth in the bone, the slide 4 can be removed or moved to one side and a screw post drilling template 24 can be fitted in the guide template slot 12. This screw post drilling template 24 will provide the proper guidance and alignment for those portions of the inline plate implant 26 that project above the bone line 30 and through the overlying soft tissue. The screw post drilling template 24 can be made from a transparent plastic and snap into the guide template slot 12 by means of flexible cantilevered projections 20 with retaining barbs. One or more vertical guiding holes 25 will allow drilling of precisely aligned holes in the underlying bone for the permucosal screw posts 28 of the inline plate implant 26. The screw posts 28 are equipped in this instance with internal threads 29 for securing artificial teeth. The inline plate implant 26 is provided with slots 27 to provide ingress of live bone for added structural integrity. Only the screw posts 28 project above the bone line 30.

Whereas the drawings and descriptions shown herein are illustrative of the mandibular region of the mouth, the apparatus described within is equally applicable to the maxillary region of the mouth and, indeed, other hard structures in the body. These and other variations of the present invention may be made which fall within the scope of the appended claims even though such variations were not related above.

The accompanying drawings referred to herein are illustrative of the invention but not restrictive thereto, and, together with the description, serve to explain the principles of the invention.

That which is claimed is:

1. Apparatus for accurately placing at least one slot in bone, the apparatus comprising, in combination:
   (a) a frame assembly having: integral side projections; a guide-slot; a captive non-rotating slide; said slide constraining the motion of a rotating cutting bit to form a narrow, flat-walled slot in said bone;
   (b) a pliable rubbery mass of quick-setting polymer, the polymer providing a firm but compliant spacer between said side projections and said bone and surrounding tissue; said polymer forming a mirror-image of the surface terrain irregularities of said bone and surrounding tissue;
   (c) the side projections of said frame assembly having means for bonding with said pliable rubbery mass of quick-setting polymer said combination assuring accurate registration and immobile placement of said frame assembly with respect to said bone and surrounding tissue; and
   (d) said frame assembly further having means to accurately distance said assembly from said bone.

2. Apparatus for accurately placing at least one slot in bone, the apparatus comprising:
   (a) a frame assembly having: integral side projections; a guide-slot; a captive non-rotating slide, said slide constraining the motion of a rotating cutting bit to form a narrow, flat-walled slot in said bone;
   (b) pliable rubbery mass of quick-setting polymer, the polymer providing a firm but compliant spacer between said side projections and said bone and surrounding tissue, said polymer forming a mirror-image mold of the surface terrain irregularities of said bone and surrounding tissue, said polymer secured to the frame; and
   (c) end stops having serrated projections as means of non-sliding engagement of said frame assembly with said bone.

3. Apparatus for accurately placing slots in bone, as recited in claim 2, in which said frame assembly further has means for Selectively mounting a fitted left and right reversible handle for a steady manual placement and firm hold on said bone.

4. Apparatus as recited in claim 3, in which a hole drilling insert is closely fitted within said guide slot, the insert having at least one aperture for accurately guiding a drill to make at least one hole in bone.

5. A method of slotting a bone to a precise width, depth and predetermined length for an inline surgical implant, the steps of the method comprising:
   (a) fabricating a guidance template frame assembly having (1) a guide-slot of predetermined length for the inline implant, (2) a captive slide, and (3) anchoring means to adjacent immobile bone structure, said frame assembly having been formed to follow the contours of said bone;
   (b) inserting a pliable rubbery mass of quick-setting polymer material between said contours and said anchoring means;
   (c) assuring, partially by use of end stops, and by application of pressure through said guidance template handle, accurate and steady manual placement of said frame assembly; and
   (d) inserting said cutting bit through a low friction bushing in a hole in said captive slide and manually drawing said cutting bit through said bone to form slot for an inline implant.

* * * * *